United States Patent
Dixon et al.

(10) Patent No.: US 11,883,823 B2
(45) Date of Patent: Jan. 30, 2024

(54) METHODS FOR THE FILTRATION OF SMALL-VOLUME HETEROGENEOUS SUSPENSIONS IN A DIGITAL MICROFLUIDIC DEVICE

(71) Applicant: THE GOVERNING COUNCIL OF THE UNIVERSITY OF TORONTO, Toronto (CA)

(72) Inventors: Christopher Alvin Dixon, Toronto (CA); Julian Lucas Lamanna, Toronto (CA); Aaron Ray Wheeler, Toronto (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 807 days.

(21) Appl. No.: 16/499,254

(22) PCT Filed: Apr. 3, 2018

(86) PCT No.: PCT/CA2018/050403
§ 371 (c)(1),
(2) Date: Sep. 28, 2019

(87) PCT Pub. No.: WO2018/176161
PCT Pub. Date: Oct. 4, 2018

(65) Prior Publication Data
US 2020/0108395 A1    Apr. 9, 2020

Related U.S. Application Data

(60) Provisional application No. 62/479,463, filed on Mar. 31, 2017.

(51) Int. Cl.
*B01L 3/00* (2006.01)
*G01N 33/80* (2006.01)

(52) U.S. Cl.
CPC ... *B01L 3/502792* (2013.01); *B01L 3/502753* (2013.01); *G01N 33/80* (2013.01);
(Continued)

(58) Field of Classification Search
None
See application file for complete search history.

(56) References Cited

U.S. PATENT DOCUMENTS

2010/0288689 A1    11/2010   Zhu
2012/0298205 A1    11/2012   Schertzer et al.
(Continued)

FOREIGN PATENT DOCUMENTS

CA    2813090 A1    4/2012
CN    101351270 A   1/2009
(Continued)

OTHER PUBLICATIONS

Kuo et al., "Decanting and mixing of supernatant human blood plasma on centrifugal microfluidic platform", Microsyst Technol (20116) 22: pp. 861-869). (Year: 2016).*
(Continued)

*Primary Examiner* — Rebecca M Giere
(74) *Attorney, Agent, or Firm* — HILLL & SCHUMACHER (57) ABSTRACT

Disclosed herein are two related techniques for digital microfluidic (DMF) processing of liquids that rely on electrostatic actuation of fluid through a strip of solid, porous media. In the first technique, droplets in a DMF device containing particles of different sizes are driven through a solid porous medium, allowing for filtering, concentration, and recovery of the particles into droplets on the basis of size. In the second technique, an aliquot of liquid media is loaded directly onto a solid porous medium, where it is wicked into a DMF device, such that the filtrate can be
(Continued)

collected into droplets. Both techniques may be useful for generating plasma from whole blood on a DMF device, an operation that will have far-reaching implications for diagnostic applications of digital microfluidics.

18 Claims, 10 Drawing Sheets

(52) U.S. Cl.
CPC ............ *B01L 2200/0668* (2013.01); *B01L 2300/0681* (2013.01); *B01L 2300/0816* (2013.01); *B01L 2300/161* (2013.01)

(56) References Cited

U.S. PATENT DOCUMENTS

| | | | |
|---|---|---|---|
| 2013/0164856 A1 | 6/2013 | Jebrail et al. | |
| 2013/0277218 A1* | 10/2013 | Mudrik | C12N 15/1006 204/601 |
| 2013/0288254 A1 | 10/2013 | Pollack et al. | |
| 2015/0253284 A1 | 9/2015 | Sudarsan et al. | |
| 2016/0274105 A1* | 9/2016 | Whitesides | G01N 33/54386 |
| 2016/0279637 A1 | 9/2016 | Sarioglu et al. | |

FOREIGN PATENT DOCUMENTS

| | | |
|---|---|---|
| CN | 102164675 A | 8/2011 |
| CN | 102861623 A | 1/2013 |
| CN | 106029231 A | 10/2016 |
| JP | 2016539331 A | 12/2016 |
| WO | 2007048111 A2 | 4/2007 |
| WO | 2010024941 A1 | 3/2010 |
| WO | 2015090863 A1 | 6/2015 |

OTHER PUBLICATIONS

Yu, Z. T. F.; Aw Yong, K. M.; Fu, J., Microfluidic Blood Cell Sorting: Now and Beyond, Small 2014, 10 (9), 1687-1703. Published Feb. 10, 2014.

Bhagat, A. A. S.; Bow, H.; Hou, H. W.; Tan, S. J.; Han, J.; Lim, C. T., Microfluidics for cell separation, Medical & Biological Engineering & Computing 2010, 48 (10), 999-1014. Published Apr. 23, 2010.

Choi, K.; Ng, A. H. C .; Fobel, R .; Wheeler, A. R., Digital Microfluidics, Annual Review of Analytical Chemistry 2012, 5(1), 413-440. Published Apr. 9, 2012.

Yang, H.; Mudrik, J. M .; Jebrail, M. J .; Wheeler, A Digital Microfluidic Method for in Situ Formation of Porous Polymer Monoliths with Application to Solid-Phase Extraction, A. R. Analytical Chemistry 2011, 83 (10), 3824-3830. Published Apr. 27, 2011.

Seale, B.; Lam, C .; Rackus, D. G.; Chamberlain, M. D .; Liu, C.; Wheeler, Digital Microfluidics for Immunoprecipitation, A. R. Analytical Chemistry 2016, 88 (20), 10223-10230. Published Oct. 4, 2016.

H. R. Nejad, E. Samiei, A. Ahmadi, M. Hoorfar, Gravity-driven hydrodynamic particle separation in digital microfluidic systems, RSC Advances 2015, 5, 35966. Published Apr. 14, 2015.

International Search Report PCT/CA2018/050403, dated Mar. 31, 2017.

* cited by examiner

Figure 1A

Figure 1Bi i) Pass mixture droplet through strip of porous material

Figure 1Bii ii) Load and dispense resuspension buffer onto DMF chip

Figure 1Biii iii) Pass buffer droplet through strip of porous material

Figure 1Biv iv) Mixture separated into two homogenous droplets

METHODS FOR THE FILTRATION OF SMALL-VOLUME HETEROGENEOUS SUSPENSIONS IN A DIGITAL MICROFLUIDIC DEVICE

FIELD

The present disclosure relates to a digital microfluidics (DMF) based method and system for filtration of small-volume heterogeneous suspensions in a digital microfluidic device.

BACKGROUND

While ubiquitous at the macroscale, the filtration and/or separation of homogenous mixtures within microfluidic devices has been the subject of recent investigation. Within the field of microfluidics, several filtration strategies have been documented—active techniques such as dielectrophoresis (DEP), magnetic, and acoustic methods (ref. 1) and passive techniques including deterministic lateral displacement, cross-flow filtration, hydrodynamic filtration, and pinched flow filtration (ref. 2). For the former (active) techniques, the equipment required to apply the required external manipulation field adds complexity and cost to the microfluidic device, while the latter (passive) techniques often require pump and valve systems and continuous flows to filter and separate particles. Another typical challenge affecting microfluidic based filtration systems is that the fabrication methods required to form the devices generally involve complicated cleanroom-based techniques as well as requiring separate design iterations to form structures capable of filtering different sizes or classes of particles.

Digital microfluidics (DMF) is a robust liquid handling technology that comprises the manipulation of discrete picolitre to microlitre-sized liquid droplets using electrostatic forces (ref. 3). DMF differs from traditional continuous flow microfluidics—rather than continuous flows within channels, droplets are sandwiched between a counter-electrode top plate and a bottom plate bearing an array of insulated driving electrodes. In this configuration, individual droplets, each serving as a distinct micro-reactor, can be dispensed, mixed, merged, and separated, making DMF a powerful sample handling and chemical processing technique. More importantly, DMF is reconfigurable—a generic device architecture can be used and re-used for virtually unlimited combinations of operations.

To date, there have been few examples of filtration and/or separation within a DMF device. One method involved porous polymer monolith (PPM) discs formed within the device for solid phase extraction (ref. 4) while other approaches have used antibody functionalized magnetic beads to separate and isolate biomolecules from complex matrices such as blood or serum (ref. 5). While successful, these methods required complex and time-consuming fabrication steps (fabrication of PPM discs), specially functionalized magnetic beads (as well as magnets mounted on stepper motors), or for samples to be diluted off-chip prior to analysis. Finally, a DMF method was developed using gravitational and hydrodynamic forces to separate particles within a device (ref. 6). However, this method was limited in scope as it required non-buoyant particles and those within a specific size range.

SUMMARY

Disclosed herein are two related techniques for DMF that rely on electrostatic actuation of fluid through a strip of solid, porous media. In technique (1), droplets in a DMF device containing particles of different sizes are driven through a solid porous medium, allowing for filtering, concentration, and recovery of the particles into droplets on the basis of size. In technique (2), an aliquot of liquid media is loaded directly onto a solid porous medium, where it is wicked into a DMF device, such that the filtrate can be collected into droplets. Both techniques may be useful for generating plasma from whole blood on a DMF device, an operation that will have far-reaching implications for diagnostic applications of digital microfluidics.

In a first embodiment, there is provided a digital microfluidics based method for filtration of heterogeneous suspensions, comprising:

a) positioning a porous material between a bottom plate and a top plate in a digital microfluidic device, the porous material having a pre-selected porosity to prevent particles larger than a pre-selected size to pass through while allowing passage therethrough of particles being smaller than said pre-selected size;

b) dispensing a droplet containing particles of different sizes onto an electrode array located on the bottom plate and actuating the electrode array in such a way as to drive the droplet through the porous material from a first side to a second side of the porous material such that the particles smaller than the pre-selected size pass through the porous material while the particles larger than the pre-selected size are trapped in the porous material or on a surface of the porous material on the first;

c) actuating the electrode array for displacing the filtered droplet away from the porous material to await further processing;

d) dispensing a droplet of resuspension buffer onto the electrode array on the second side of the porous material and actuating the electrode array so as to drive the droplet of resuspension buffer through the porous material from the second side to the first side so that the larger trapped particles are freed from the porous material and suspended into the droplet of resuspension buffer; and e) actuating the electrode array for displacing droplet of resuspension buffer away from the porous material to await further processing.

In a second embodiment, there is provided a digital microfluidics based method for filtration of heterogeneous suspensions, comprising: a) positioning a porous material between a bottom plate and a top plate in a digital microfluidic device, the porous material having a pre-selected porosity to prevent particles larger than a pre-selected size to pass through while allowing passage therethrough of particles being smaller than said pre-selected size, the porous material having a loading section that extends beyond an edge of the top plate;

b) dispensing a sample droplet containing particles of different sizes onto the loading section of the porous material such that the sample droplet is wicked into the porous material;

c) dispensing a reagent onto an electrode array located on the bottom plate and actuating the electrode array in such a way as to drive the droplet through the porous material from a first side to a second side of the porous material such that the particles smaller than the pre-selected size pass out of the porous material to give a particle loaded reagent droplet with the smaller particles on the second side while the particles larger than the pre-selected size remain trapped in the porous material; and c) actuating the electrode array for displacing the particle loaded reagent droplet away from the porous material to await further processing.

A further understanding of the functional and advantageous aspects of the present disclosure can be realized by reference to the following detailed description and drawings.

BRIEF DESCRIPTION OF THE DRAWINGS

Embodiments will now be described, by way of example only, with reference to the drawings, in which:

FIG. 1B(i) to 1B(iv) shows a sequence of the device of FIG. 1A implementing different steps in the separation process disclosed herein;

FIG. 2B(i) to 2B(iii) shows a sequence of the device of FIG. 2A implementing different steps in the separation process disclosed herein;

FIG. 2C(i) to FIG. 2C(ii) shows photographs depicting the sequence of a separation experiment using the DMF device of FIG. 2A;

DETAILED DESCRIPTION

Various embodiments and aspects of the disclosure will be described with reference to details discussed below. The following description and drawings are illustrative of the disclosure and are not to be construed as limiting the disclosure. The Figures are not to scale. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art.

As used herein, the term "particle" in the context of the present disclosure means anything in the fluid medium that can be distinguished from the bulk fluid, including cells.

In technique (1), particles are filtered from a droplet by applying voltages to a series of electrodes that force the droplet though a liquid-saturated strip of porous material, anchored at each end with a hydrophobic barrier and sandwiched in between the top and bottom plates of a DMF device. Particles with diameters greater than the pore size of the porous medium become trapped on the strip, while the liquid (including suspensions of particles with diameters smaller than the pore size of the porous medium) is passed through to the other side. The particles trapped on the filter can then be collected by passing a fresh droplet back through the strip in the opposite direction. By tuning the number (and volume) of droplets moving each way through the porous medium, particles can be concentrated or diluted.

Figure 1:
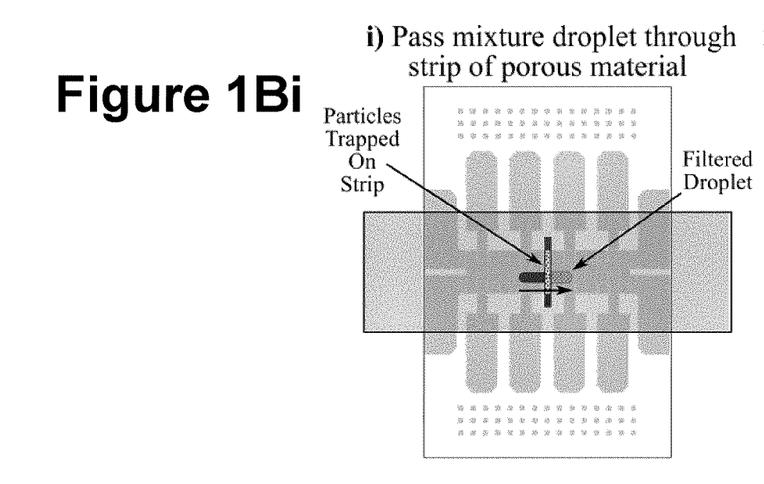
Figure 1A:
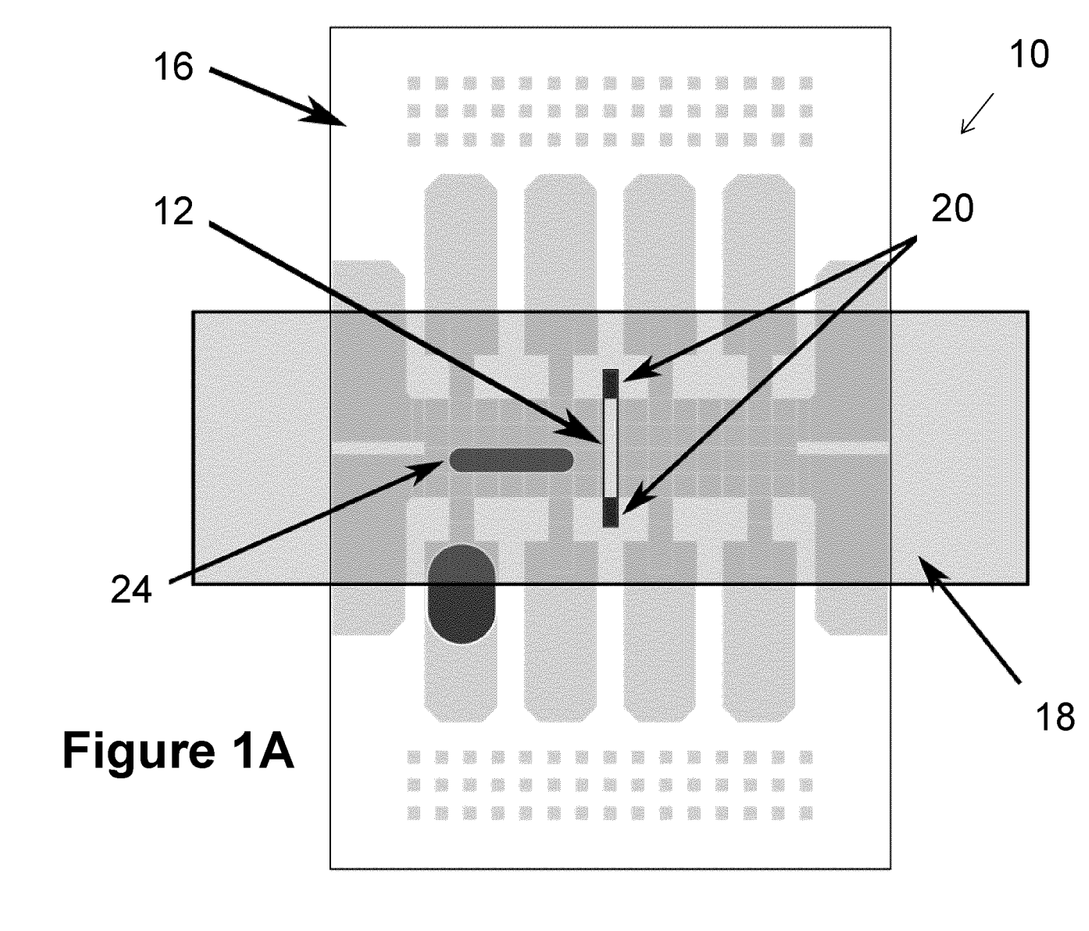
FIG. 1A shows a DMF device modified to include a porous membrane for separating different sized particles in a fluid.

FIG. 1A shows a DMF device 10 modified to include a porous material 12 for separating different sized particles in a fluid. The fluid and porous material 12 are sandwiched in between a DMF bottom plate 16 bearing an array of driving electrodes and a top plate counter electrode 18. The porous material 12 may be any medium containing pores smaller than the particles to be separated. Porous material 12 includes hydrophobic anchors 20 located at the ends of the material to prevent liquid wicking around the ends of the material 12. Non-limiting examples of the porous material 12 include porous membranes that are polymer based, fiber based or some combination of the two. FIG. 1A shows a droplet 24 positioned to be filtered.

Figure 1C:
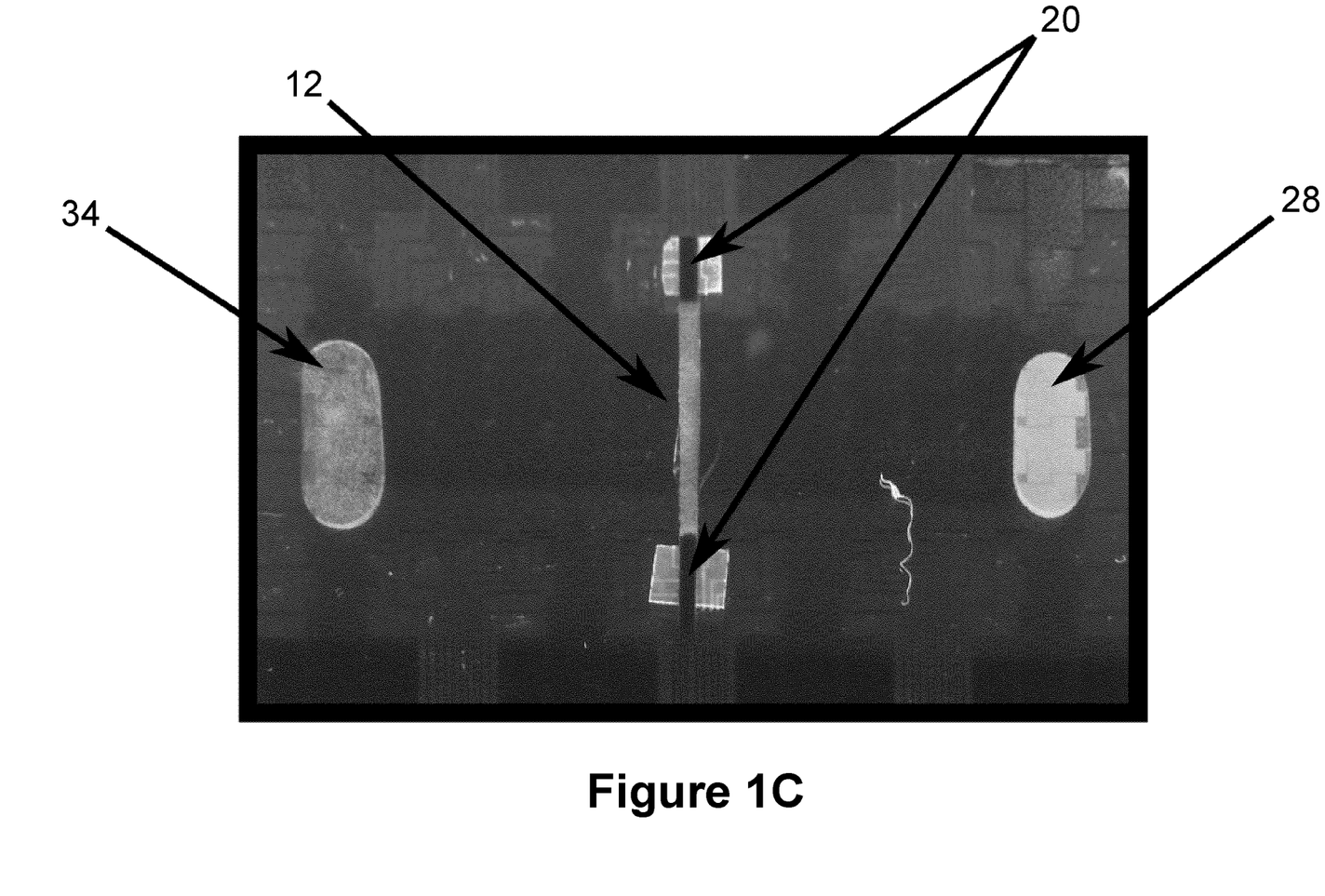
FIG. 1C shows a photograph (collected under UV illumination) depicting the outcome of a particle separation experiment using the DMF device of FIGS. 1A and 1B.

An exemplary illustration of technique (1) is shown in FIG. 1B, and preliminary data are shown in FIG. 1C. In the latter, a droplet containing a mixture of red and green fluorescent beads having diameters of 0.3 μm and 10 μm, respectively, were processed on a DMF device 10 using technique (1). The strip of porous material 12 had pore sizes such that the green 10 μm particles became trapped, while the droplet and the smaller red particles passed through (28). The green particles were then collected into a fresh droplet of buffer (34).

More particularly, FIG. 1A, 1B and 1C illustrates technique (1) in which FIG. 1A to 1B(iv) illustrate the steps of droplet filtration and particle resuspension on a DMF device. In FIG. 1A, as discussed above, the strip of porous material 12 is anchored at both ends with hydrophobic barriers 20 to either the top- or bottom-plate of the DMF device 10 (in this case, via paraffin wax) and assembled such that the medium 12 is between the top and bottom plates 18 and 16 respectively. The droplet 24 has been dispensed and ready to be filtered, being shown on the left hand side of porous material 12. The droplet 24 to be filtered is dispensed and actuated by applying a series of voltages to the bottom plate 16 electrodes. In FIG. 1B(i), as the droplet passes though the porous material 12, the particles being unable to pass through material 12 are trapped on the strip while filtrate continues to the other side containing any smaller particles having a size less than the pore size of the porous material 12. In FIG. 1B(ii) the particles are shown trapped in the porous material 12 and the filtered droplet 28 is displaced away from the porous material 12 shown to the right hand side of porous strip 12. In FIG. 1B(iii), to collect the trapped particles, a droplet 32 of resuspension buffer is dispensed and actuated towards the porous strip material 12 from the opposite direction (right hand side to the left hand side of strip 12). In FIG. 1B(iv), as buffer passes though the strip, the trapped particles are freed from the strip 12 and suspended into droplet 34.

FIG. 1C shows a photograph (collected under UV illumination) depicting the outcome of a particle separation experiment. First, a droplet containing a mixture of 0.3 µm diameter particles and larger 10 µm diameter particles was passed from left-to-right through the strip of porous material 12 anchored at both ends with hydrophobic barriers 20. The resulting filtrate droplet 28 is visible on the right hand side of the photograph which contains the 0.3 µm diameter particles. Second, a droplet of buffer was dispensed and passed from right-to-left through the strip which released the larger particles trapped in the porous material and the resulting droplet 34 is visible on the left hand side of the photograph.

Technique (2), like technique (1), relies on a strip of porous, solid medium in a DMF device. But in Technique (2), the liquid suspension to be filtered is loaded directly into the porous medium (which may simply be the "edge" of the strip, or a separate "membrane" that is laminated to the edge of the strip). As the solution wicks through the stationary medium, particles with diameter larger than the pore size of the stationary material become trapped on top or within the medium while the fluid flows into the strip via capillary force. A droplet of buffer is then passed through the strip to collect solutes or small particles.

Figure 2:
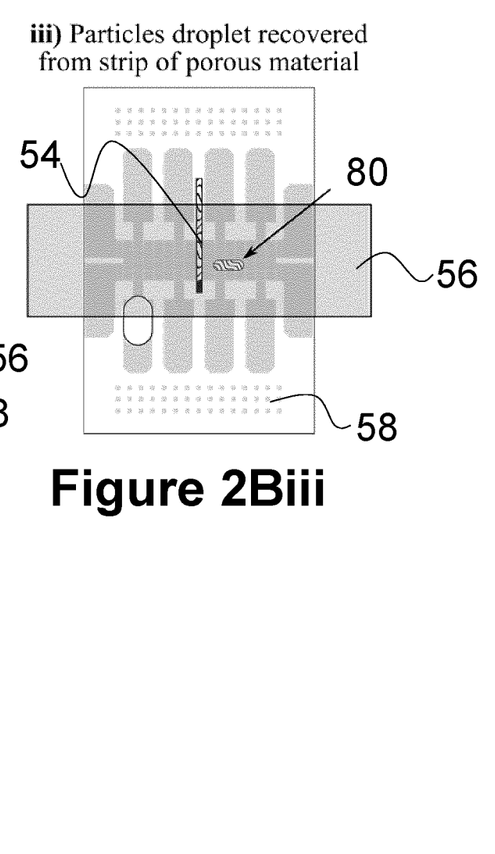
Figure 2A:
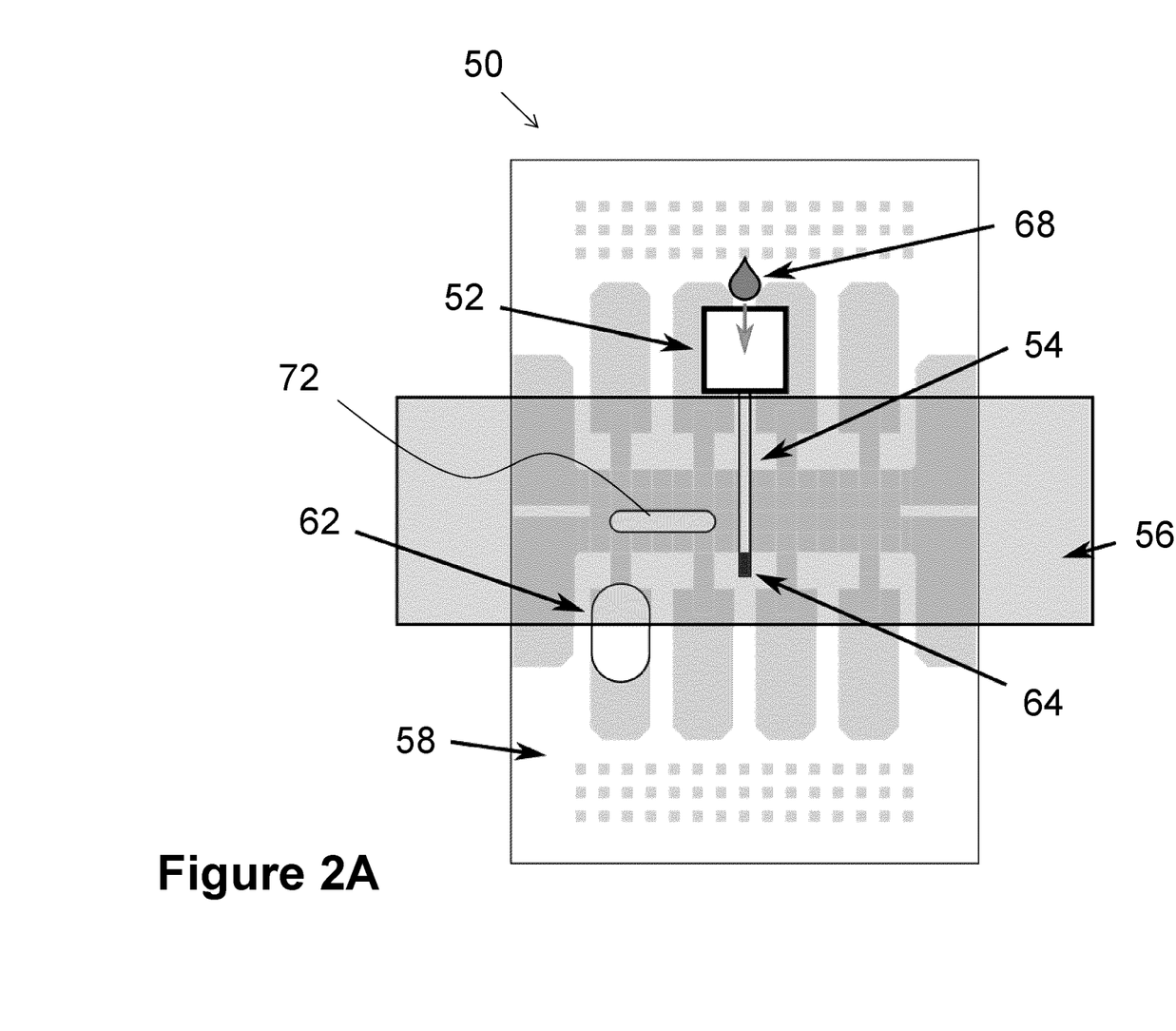
FIG. 2A shows another embodiment of a DMF device modified to include two porous membranes for separating different sized particles in a fluid.

FIG. 2A shows another embodiment of a DMF device 50 modified to include two porous membranes 52 and 54 for separating different sized particles in a fluid. In this embodiment a porous membrane 54 having a hydrophobic anchor 64 is placed in between the top and bottom plates 56 and 58 of the DMF device 50, with one end extending beyond the edge of the top plate 56. A second separating membrane 52 is laminated on top of the first, porous membrane 54 outside of the top plate 56. The porous membrane 54 acts as a medium to transport separated fluid into the DMF device 50 where it is later recovered. A droplet 68 containing a particle suspension to be separated is fed into the separation membrane 52 as shown in FIG. 2A. A source of resuspension buffer 62 is located so that upon the need for the buffer, a droplet 72 can be moved beside the porous material 54 as shown on the left hand side of the material 54 in FIG. 2A. The purpose of the separation membrane 52 is to allow for direct application of the particle suspension 68 to be filtered on the device without any prior preprocessing and to capture all undesired particles present in the suspension 68 while allowing other desired components to move into the porous strip 54 via capillary action.

Figure 2D:
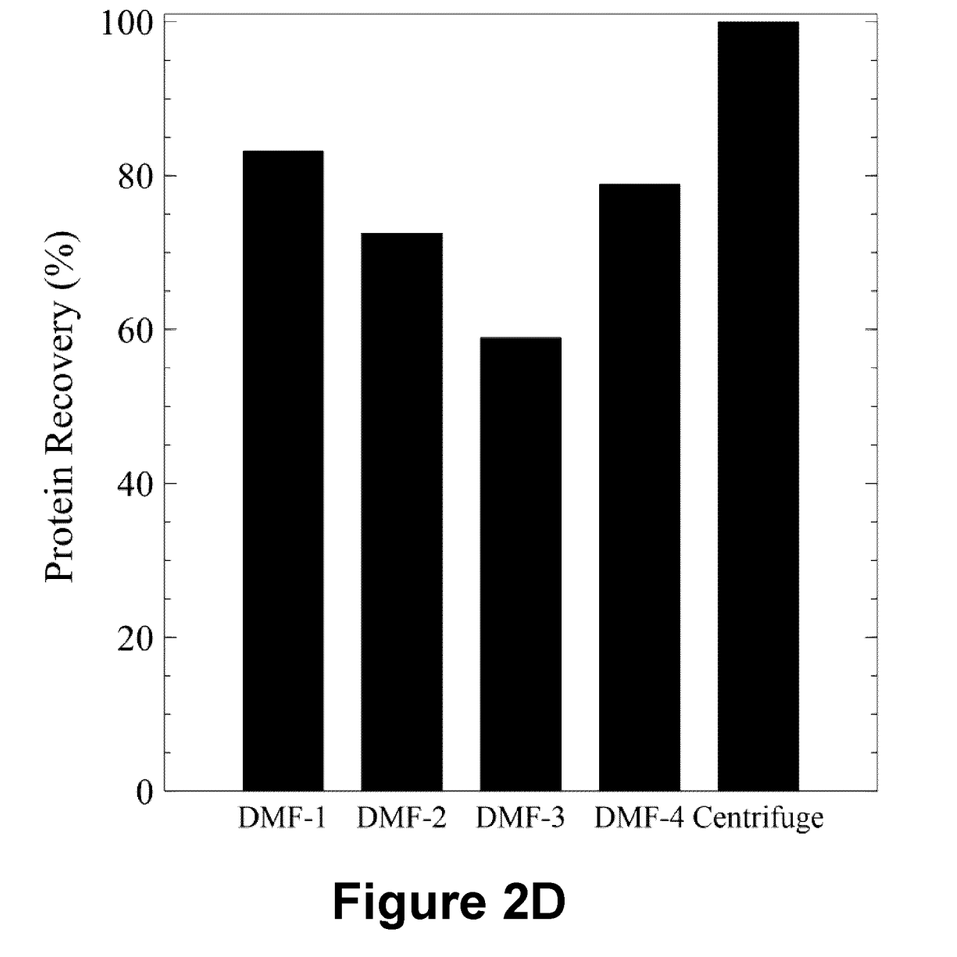
FIG. 2D shows representative results for whole blood aliquots treated as shown in the sequence of FIG. 2B.
Figure 2E:
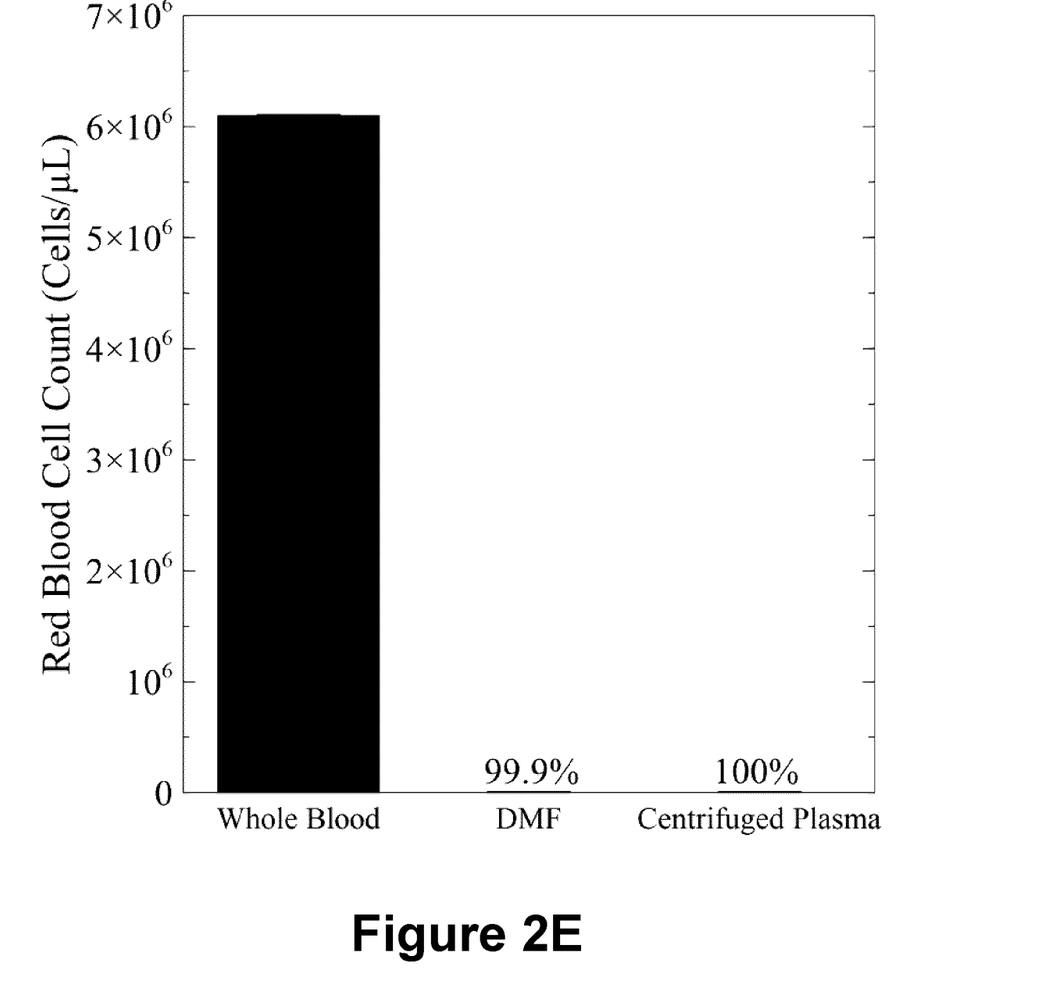
FIG. 2E shows the relative purity (count of red blood cells) of whole blood aliquots treated as shown in the sequence of FIG. 2B compared to untreated whole blood.

An exemplary illustration of process (2) is shown in FIGS. 2B(i) to 2B(iii), and preliminary data are shown in FIGS. 2C, 2D and 2E. FIG. 2C(i) shows a photograph where a 50 µL aliquot of dyed buffer was loaded onto DMF device 50, saturating porous membranes 52 and 54 with dye. A fresh droplet 62 of undyed buffer was passed left-to-right through porous membrane 54 collecting dyed liquid (as in FIG. 2B(iii)). FIG. 2C(ii) shows the resulting extracted droplet (80) which is visible on the right hand side of the photograph which contains the blue dye. An area of porous membrane 54 depleted of blue dye is also visible.

In both FIGS. 2D and 2E, 50 µL aliquots of whole blood were loaded onto DMF device 50, where the cells and other particles became trapped in the membrane 52. Fresh droplets of buffer were used to collect plasma (as in FIG. 2B(iii)), which were then evaluated for protein content using a protein assay kit by measuring the optical density at 620 nm. For reference, the protein content recovered using the gold-standard plasma-separation technique, centrifugation, is also shown. Protein recovery is the ratio of protein concentration between plasma droplets generated from whole blood aliquots treated as shown in the sequence of FIG. 2B and the gold-standard technique respectively.

The purity of generated plasma droplets is measured by counting the number of red blood cells remaining after treating whole blood aliquots using the sequence shown in FIG. 2B. For reference, the red blood cell count in whole blood is also shown. Separation efficiency is the percentage of red blood cells removed. These data are preliminary; we are confident that by tuning the volume of blood, the size of the membrane and porous material, and the number and volume of recovery droplets, the new technique will be capable of comparable recovery rates to the gold-standard technique, all on a simple, handheld DMF device operated with no moving parts. In addition, preliminary evidence (not shown here) suggests that the hemolysis levels observed for the new technique are comparable or lower to those observed for the gold-standard.

More particularly, FIGS. 2A, 2B(i) to 2B(iii), 2D and 2E illustrate technique (2) in which FIGS. 2A to 2B(iii) illustrates the steps of filtration on a DMF device. In FIG. 2A, the strip of porous material 54 is anchored at one end with a hydrophobic barrier 64 to either the top- or bottom-plate 56, 58 respectively, of DMF device 50 (in this case, via paraffin wax) and assembled such that the medium is between the top and bottom plates 56, 58 of DMF device 50. The strip 54 geometry is designed such that one end extends beyond the boundary of the top plate 56. If needed, an extra separation-membrane 52 can be laminated to the free end of the strip. In FIG. 2B(i), an aliquot 68 of a suspension of solids is loaded onto the membrane/strip 52, such that the fluid wicks into the device 50, saturating the porous material 54. In FIG. 2B(ii), a buffer droplet 72 is passed through the strip of porous material 54 by applying a series of voltages to the bottom plate 58 electrodes. In FIG. 2B(iii), a suspension of solutes (and/or a suspension of particles with diameter smaller than the pore size of the membrane/medium 54) is collected into the droplet 80.

FIG. 2D shows representative results for whole blood aliquots treated as shown in FIGS. 2B(i) to 2B(iii). The protein recovery represents the amount of protein in a plasma sample compared to plasma generated using the gold-standard centrifugation technique. "DMF-1", "DMF-2", DMF-3" and "DMF-4" represent plasma droplets recovered from separate blood aliquots on DMF devices, while "Centrifuge" is plasma recovered by the gold-standard centrifugation technique. Protein recovery for "DMF-1", "DMF-2", DMF-3" and "DMF-4" are corrected to account for the volume of plasma extracted from porous membrane 54.

FIG. 2E shows data for the separation efficiency of the process outlined in FIGS. 2B(i) to 2B(iii). Briefly, 50 µL aliquots of whole blood were loaded onto DMF device 50, where the cells and other particles became trapped in the membrane 52. Fresh droplets of buffer were used to collect plasma (as in FIG. 2B(iii)), and a hemocytometer was used to count the red blood cells (RBCs) in the recovered plasma droplet (200 RBCs/µL). For reference, the RBC count for whole blood (6.1×10⁶ RBCs/μL) and for plasma recovered by centrifugation techniques (0 RBCs/μL) is shown. Separation efficiency is the percentage of RBCs removed by either DMF or gold-standard centrifugation processes and is also shown.

Figure 3:
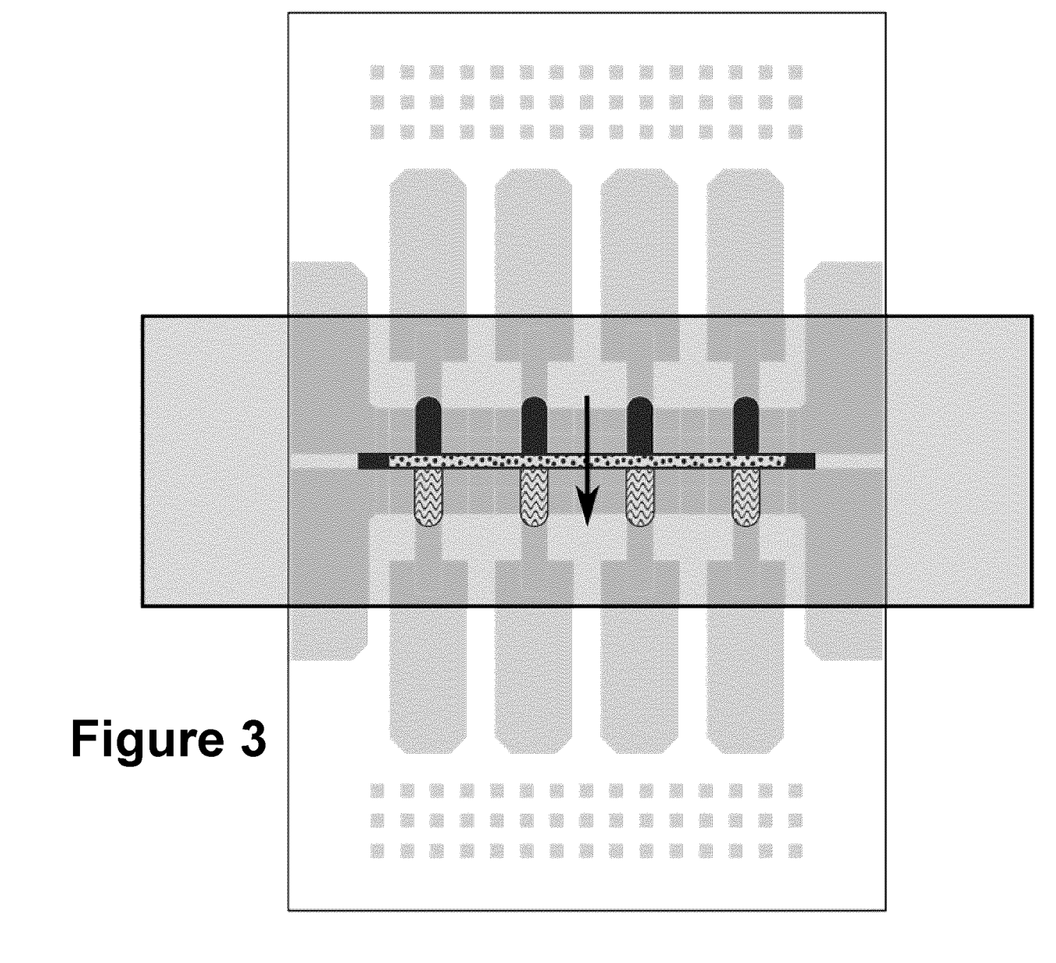
FIG. 3 shows another embodiment of a DMF device modified to include a porous membrane for separating different sized particles in a fluid located in a different orientation compared to the DMF device of FIG. 1A.

FIG. 3 shows another embodiment of a DMF device 70 modified to include a porous membrane strip 72 for separating different sized particles in a fluid located in a different orientation compared to the DMF device 10 of FIG. 1A. The porous strip 72 has been made longer and rotated 90 degrees in device 70 in comparison to the orientation of strip 54 in device 10 of FIG. 1A to allow for multiplex separation.

Figure 4:
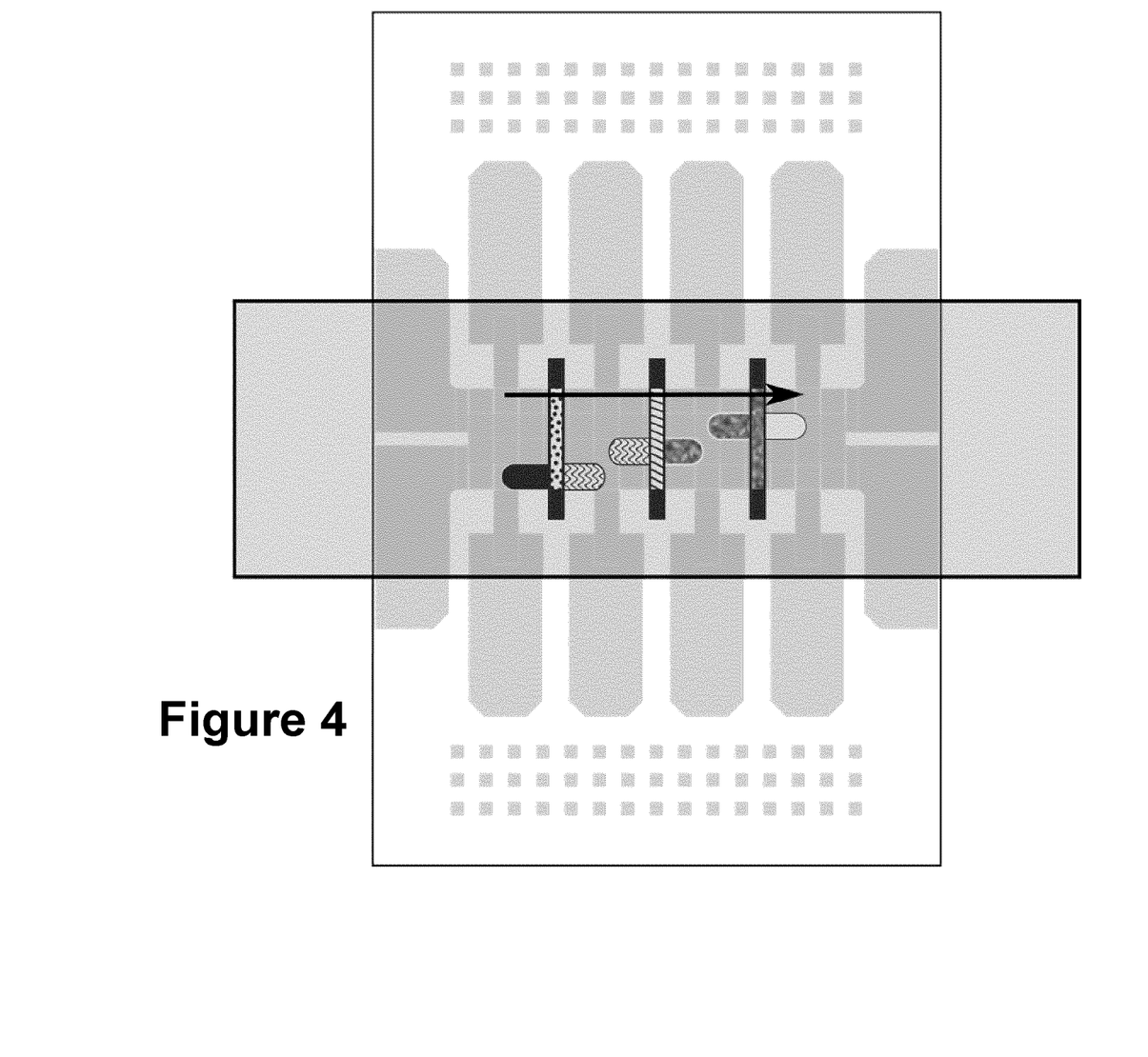
FIG. 4 shows another embodiment of a DMF device modified to include multiple serially positioned porous membranes for separating multiple differently sized particles in a fluid.

FIG. 4 shows another embodiment of a DMF device 90 modified to include multiple serially positioned porous membranes 92 for separating multiple differently sized particles in a fluid. The membranes 92 are placed in the device 90 arranged based on decreasing pore size to sequentially filter particles which may be recovered later.

The above discussion has referred to the DMF device as having the lower plate holding the DMF electrodes while the upper plate is the counter electrode. In an alternative embodiment of the present method a one-plate DMF device where the driving electrodes and counter electrode are coplanar may be used. The one-plate device differs from the two-plate device in how the voltages are applied. Instead of applying the driving voltage to the bottom plate and the ground voltage to the top plate, the driving and ground voltages are both applied to adjacent electrodes on the bottom plate. In this embodiment, the procedure remains the same as what was described above. The top plate is still required but it is not serving the role of counter electrode.

The foregoing description of the preferred embodiments of the disclosure has been presented to illustrate the principles of the disclosure and not to limit the disclosure to the particular embodiment illustrated. It is intended that the scope of the disclosure be defined by all of the embodiments encompassed within the following claims and their equivalents.

REFERENCES (1) Yu, Z. T. F.; Aw Yong, K. M.; Fu, J. *Small* 2014, 10 (9), 1687-1703.
(2) Bhagat, A. A. S.; Bow, H.; Hou, H. W.; Tan, S. J.; Han, J.; Lim, C. T. *Medical & Biological Engineering & Computing* 2010, 48 (10), 999-1014.
(3) Choi, K.; Ng, A. H. C.; Fobel, R.; Wheeler, A. R. *Annual Review of Analytical Chemistry* 2012, 5 (1), 413-440.
(4) Yang, H.; Mudrik, J. M.; Jebrail, M. J.; Wheeler, A. R. *Analytical Chemistry* 2011, 83 (10), 3824-3830.
(5) Seale, B.; Lam, C.; Rackus, D. G.; Chamberlain, M. D.; Liu, C.; Wheeler, A. R. *Analytical Chemistry* 2016, 88 (20), 10223-10230.
(6) H. R. Nejad, E. Samiei, A. Ahmadi, M. Hoorfar, *RSC Advances* 2015, 5,35966.

Therefore what is claimed is:

1. A digital microfluidics based method for filtration of heterogeneous suspensions, comprising:
    a) positioning a porous material between a bottom plate and a top plate in a digital microfluidic device, the porous material having a pre-selected porosity to prevent particles larger than a pre-selected size to pass through while allowing passage therethrough of particles being smaller than said pre-selected size;
    b) dispensing a droplet containing particles of different sizes onto an electrode array located on the bottom plate and actuating the electrode array in such a way as to drive the droplet through the porous material from a first side to a second side of the porous material such that the particles smaller than the pre-selected size pass through the porous material to form a filtered droplet while the particles larger than the pre-selected size are trapped in the porous material or on a surface of the porous material on the first side;
    c) actuating the electrode array for displacing the filtered droplet away from the porous material to await further processing;
    d) dispensing a droplet of resuspension buffer onto the electrode array on the second side of the porous material and actuating the electrode array so as to drive the droplet of resuspension buffer through the porous material from the second side to the first side of the porous material so that the larger trapped particles are freed from the porous material and suspended into the droplet of resuspension buffer on the first side of the porous material; and
    e) actuating the electrode array for displacing the droplet of resuspension buffer away from the porous material to optionally await further processing,
    wherein the porous material is an elongated strip of porous material having a length defined by elongated opposed sides and opposed ends,
    wherein the method comprises preventing liquid exiting at least one of the opposed ends by providing the at least one of the opposed ends with a non-porous hydrophobic material embedded therein and, the elongated opposed sides being devoid of the non-porous hydrophobic material, and
    wherein the non-porous hydrophobic material has hydrophobicity higher than that of said porous material, and the non-porous hydrophobic material is anchoring the strip of porous material to the top and/or bottom plate.

2. The method according to claim 1, wherein both the opposed ends include the non-porous hydrophobic material embedded therein to prevent liquid exiting the opposed ends.

3. The method according to claim 1, wherein the electrode array located on the bottom plate comprises driving electrodes and counter electrodes, such that the digital microfluidic device is for one-plate operation.

4. The method according to claim 1, wherein the electrode array located on the bottom plate comprises driving electrodes, and the digital microfluidic device further comprises counter electrodes located on the top plate, such that the digital microfluidic device is for two-plate operation.

5. The method according to claim 1, wherein the porous material is two or more strips of porous material arranged sequentially in the digital microfluidic device such that droplets are passed through the two or more strips of porous material with the strips of porous material selected to have decreasing pore sizes for filtering droplets having a plurality of different sizes.

6. The method according to claim 1, wherein the droplet is a droplet of human or animal fluid.

7. The method according to claim 6, wherein the droplet is a droplet of human blood, human semen and urine.

8. The method according to claim 6, wherein the droplet is a droplet of human blood, and wherein the method is configured for generating plasma from whole blood.

9. A digital microfluidics based method for filtration of heterogeneous suspensions, comprising:
    a) positioning a porous material between a bottom plate and a top plate in a digital microfluidic device, the porous material having a pre-selected porosity to prevent particles larger than a pre-selected size to pass through while allowing passage therethrough of particles being smaller than said pre-selected size, the porous material having a loading section that extends beyond an edge of the top plate;

b) dispensing a sample droplet containing particles of different sizes onto the loading section of the porous material such that the sample droplet is wicked into the porous material;

c) dispensing a reagent onto an electrode array located on the bottom plate and actuating the electrode array in such a way as to drive the droplet through the porous material from a first side to a second side of the porous material such that the particles smaller than the pre-selected size pass out of the porous material to give a particle loaded reagent droplet with the smaller particles on the second side while the particles larger than the pre-selected size remain trapped in the porous material; and c) actuating the electrode array for displacing the particle loaded reagent droplet away from the porous material to await further processing, wherein the porous material is an elongated strip of porous material having a length defined by elongated opposed sides and opposed ends, and wherein the method comprises preventing liquid exiting an end of the porous strip opposite the loading section by providing said end of the porous strip opposite the loading section with a non-porous hydrophobic material embedded therein, and the elongated opposed sides being devoid of the non-porous hydrophobic material, wherein the non-porous hydrophobic material has hydrophobicity higher than that of said porous material, and the non-porous hydrophobic material is anchoring the strip of porous material to the top and/or bottom plate.

10. The method according to claim 9, including a separation-membrane can laminated to the loading section having a preselected porosity onto which the sample reagent is loaded.

11. The method according to claim 9, wherein the digital microfluidic device is configured for one-plate operation.

12. The method according to claim 9, wherein the digital microfluidic device is configured for two-plate operation.

13. The method according to , claim 9 wherein the droplet is a droplet of human or animal fluid.

14. The method according to claim 13, wherein the droplet is a droplet of human blood, human semen and urine.

15. The method according to claim 14, wherein the droplet is a droplet of human blood, and wherein the method is configured for generating plasma from whole blood.

16. The method according to claim 2, wherein the electrode array located on the bottom plate comprises driving electrodes and counter electrodes, such that the digital microfluidic device is for one-plate operation.

17. The method according to claim 2, wherein the electrode array located on the bottom plate comprises driving electrodes, and the digital microfluidic device further comprises counter electrodes located on the top plate, such that the digital microfluidic device is for two-plate operation.

18. The method according to claim 1, wherein the non-porous hydrophobic material is wax.

* * * * *